United States Patent
Brumar et al.

(10) Patent No.: US 11,795,128 B2
(45) Date of Patent: Oct. 24, 2023

(54) METHODS OF SYNTHESIZING CANNABIGEROL, CANNABIGEROLIC ACID, AND ANALOGS THEREOF

(71) Applicant: Canopy Growth Corporation, Smiths Falls (CA)

(72) Inventors: Daniel Brumar, Smiths Falls (CA); Mahmood Azizpour Fard, Smiths Falls (CA); Ben Geiling, Smiths Falls (CA); Mohammadmehdi Haghdoost Manjili, Smiths Falls (CA)

(73) Assignee: CANOPY GROWTH CORPORATION

( * ) Notice: Subject to any disclaimer, the term of this patent is extended or adjusted under 35 U.S.C. 154(b) by 0 days.

(21) Appl. No.: 17/883,571

(22) Filed: Aug. 8, 2022

(65) Prior Publication Data
US 2023/0039312 A1 Feb. 9, 2023

Related U.S. Application Data

(63) Continuation of application No. 17/699,748, filed on Mar. 21, 2022, now Pat. No. 11,643,380, which is a (Continued)

(51) Int. Cl.
*C07C 37/16* (2006.01)
*B01J 31/02* (2006.01)
(Continued)

(52) U.S. Cl.
CPC ............ *C07C 37/16* (2013.01); *B01J 21/04* (2013.01); *B01J 21/16* (2013.01); *B01J 27/128* (2013.01); *B01J 31/0229* (2013.01)

(58) Field of Classification Search
CPC ...... B01J 31/0229; B01J 27/128; B01J 21/04; B01J 21/16; C07C 37/16
(Continued)

(56) References Cited

U.S. PATENT DOCUMENTS 11,384,040 B2 * 7/2022 Brumar ............... C07C 51/00
2010/0298579 A1 11/2010 Steup et al.
(Continued)

FOREIGN PATENT DOCUMENTS

CA 2866787 A1 * 4/2013 ............ A61P 17/00
CA 2902452 A1 9/2014
(Continued)

OTHER PUBLICATIONS

Raphael Mechoulam et al., "Carboxylation of Resorcinols with Methylmagnesium Carbonate. Synthesis of Cannabinoid Acids." Chemical Communications, 228, pp. 343-344. (Year: 1969).*
(Continued)

*Primary Examiner* — Patricia L. Hailey
(74) *Attorney, Agent, or Firm* — Bracewell LLP; Brad Y. Chin

(57) ABSTRACT

Disclosed are methods for preparing cannabigerol (CBG) or a CBG analog, embodiments of the method comprising providing a compound (I); combining the compound (I) with geraniol and a solvent to form a reaction mixture; and combining the reaction mixture with an acid catalyst to form a product mixture comprising the CBG or the CBG homolog. The method may further comprise separating the CBG or the CBG analog from the product mixture and may further comprise purifying the CBG or CBG analog. Methods for preparing cannabigerolic acid (CBGA) or a cannabigerolic acid analog are also disclosed. The present disclosure also provides highly purity CBG, CBGA, and analogs thereof.

19 Claims, 10 Drawing Sheets

Related U.S. Application Data continuation of application No. 17/495,058, filed on Oct. 6, 2021, now Pat. No. 11,384,040, which is a continuation of application No. PCT/CA2021/050651, filed on May 11, 2021.

(60) Provisional application No. 63/023,400, filed on May 12, 2020.

(51) Int. Cl.
*B01J 27/128* (2006.01)
*B01J 21/16* (2006.01)
*B01J 21/04* (2006.01)

(58) Field of Classification Search
USPC .......................................................... 568/766
See application file for complete search history.

(56) References Cited

U.S. PATENT DOCUMENTS

| | | | |
|---|---|---|---|
| 2017/0283837 A1* | 10/2017 | Kavarana | ............. C12Y 121/03 |
| 2017/0298399 A1 | 10/2017 | Peet et al. | |
| 2020/0115306 A1 | 4/2020 | Smeltzer et al. | |
| 2020/0223814 A1* | 7/2020 | Nivorozhkin | ........ A61M 11/041 |
| 2021/0276936 A1 | 9/2021 | Smeltzer et al. | |
| 2021/0380513 A1 | 12/2021 | Magolan et al. | |

FOREIGN PATENT DOCUMENTS

| | | | | |
|---|---|---|---|---|
| CA | | 3081858 A1 | 11/2021 | |
| WO | WO-2014134281 A1 * | | 9/2014 | ............... A01H 6/28 |
| WO | WO-2018209143 A1 * | | 11/2018 | ............... C12N 9/88 |
| WO | | 2019033164 A1 | 2/2019 | |
| WO | | 2020092823 A1 | 5/2020 | |
| WO | WO-2020101731 A1 * | | 5/2020 | ............. C07B 63/04 |

OTHER PUBLICATIONS

Baek, et al., Bonon Trifluoride Etherate on Alimina—A Modified Lewis Acid Reagent. An Improved Synthesis of Cannabidiol, Tetrahedron Letters, vol. 26, No. 8, pp. 1083-1086, 1995.

CA3132439 Office Action dated Jan. 14, 2022, 4 pgs.

Citti, et al., A novel phytocannabinoid isolated from *Cannabis sativa* L. with an invivo cannabimimetic activity higher than tetrahydrocannabinol: Tetrahydrocannabiphorol, Scientific Reports, (2019) 9:20335, 13 pages.

Conference Presentation by J. Magolan "Chemical Synthesis of Cannabinoids", Meeting of the McMaster's Center for Medicinal Cannabis Research, Hamilton, Ontario, Jun. 7, 2019.

Jentsch, et al., Efficient Synthesis of Cannabigerol, Grifolin, and Piperogalin via Alumina-Promoted Allylation, Journal of Natural Products, vol. 83, pp. 2587-2591, 2020.

Jentsch, Synthesis of Cannabigerol Derivatives via Direct ortho-allylation of phenols, Postdoctoral Fellow, McMaster University, Canada, National ASC Meeting and Exposition, Aug. 27, 2019, 29 pgs.

PCT/CA2021/050651 International Search Report and Written Opinion dated Jul. 16, 2021, 13 pages.

Zhang, Alumina Directed Ortho Allylation of Phenois: A Thesis Submitted to the School of Graduate Studies in Partial Fulfilment of the Requirements for the Degree Doctor of Philosophy, Copyright McMaster University, Aug. 2020.

* cited by examiner

METHODS OF SYNTHESIZING CANNABIGEROL, CANNABIGEROLIC ACID, AND ANALOGS THEREOF

CROSS-REFERENCE TO RELATED APPLICATIONS

This application is a continuation application of Ser. No. 17/699,748, filed Mar. 21, 2022, titled, "METHODS OF SYNTHESIZING CANNBIGEROL, CANNABIGEROLIC ACID, AND ANALOGS THEREOF, which is a continuation application of Ser. No. 17/495,058, filed on Oct. 6, 2021, titled, "METHODS OF SYNTHESIZING CANNBIGEROL, CANNABIGEROLIC ACID, AND ANALOGS THEREOF, which is a continuation application of International Application No. PCT/CA2021/050651, filed on May 11, 2021, titled, "METHODS OF SYNTHESIZING CANNBIGEROL, CANNABIGEROLIC ACID, AND ANALOGS THEREOF," which claims the benefit of and priority to U.S. Provisional Patent Application Ser. No. 63/023,400, filed on May 12, 2020, of which are hereby incorporated by reference in their entirety.

TECHNICAL FIELD

The present disclosure generally relates to methods of synthesizing cannabigerol (CBG), cannabigerolic acid (CBGA), and analogs thereof, including compositions having enhanced concentrations of these compounds.

BACKGROUND

Cannabinoids are often defined in pharmacological terms as a class of compounds that exceed threshold-binding affinities for specific receptors found in central nervous system tissues and/or peripheral tissues. The interactions between cannabinoids and their receptors are under active investigation because the resultant effects are demonstrably important both in medicinal and reactional contexts.

The length of the alkyl side chain on the resorcinol moiety of certain cannabinoids has been shown to impact biological activity. For example, studies have shown that $\Delta^9$-tetrahydrocannabinol ($\Delta^9$-THC) requires a minimum of a three-carbon chain (i.e. tetrahydrocannabivarin; THCV) for cannabinoid receptor CB1 binding. Binding affinity increases with side chain length to a peak affinity at an eight-carbon chain. It has been reported that seven-carbon alkyl chain homologs of cannabidiol (CBD) and $\Delta^9$-THC, respectively named cannabidiphorol (CBDP) and tetrahydrocannabiphorol (THCP), can be isolated from cannabis plant material in very small quantities (<1 mg in 10 g of cannabis plant material).

Cannabigerol (CBG) is a non-psychoactive cannabinoid that displays numerous potential health benefits, including the following: functioning as a neuroprotectant; antioxidant properties; aiding with skin ailments as an antibacterial and antifungal agent; appetite stimulation; treatment of gastrointestinal disorders; inflammation reduction; and lowering intraocular pressure, which may benefit glaucoma patients. CBG may also be used for recreational purposes.

The acidic derivative of CBG, cannabigerolic acid (CBGA), plays a vital role in the biochemistry of the cannabis plant. CBGA is a critical precursor in the formation of cannabinoids such as tetrahydrocannabinolic acid A (THCA), cannabidiolic acid (CBDA), cannabichromenic acid (CBCA), and CBG.

Despite wide-ranging potential applications, CBG and CBGA, and analogs thereof, are not currently used at scale. CBG and CBGA are typically found in low concentrations in cannabis plant material, extracts, and distillates and/or the like. Separating CBG or CBGA from such compositions can pose significant challenges as CBG has similar properties and characteristics (e.g. solubility and/or affinity profile) to a number of other cannabinoids. Similarly, CBG can be difficult to separate from reaction mixtures. Therefore, isolation of CBG from a cannabis plant is a challenging, costly, and time-consuming process, rendering large-scale quantities of CBG or CBGA effectively inaccessible.

Accordingly, alternate methods for producing and obtaining CBG, CBGA and analogs thereof are desirable, particularly in large quantities.

SUMMARY

The present disclosure relates to methods of synthesizing cannabigerol (CBG), cannabigerolic acid (CBGA), and analogs thereof.

In one aspect, the present disclosure relates to a method for preparing CBG or a CBG analog, the method comprising: providing a compound (I) of the following structure:

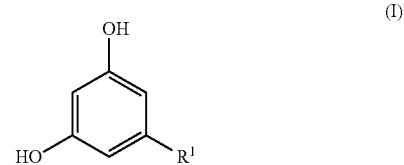

wherein $R^1$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}$ and $R^{2b}$ are each independently hydrogen or $C_1$-$C_6$ alkyl; combining the compound (I) with geraniol and a solvent to form a reaction mixture; and combining the reaction mixture with an acid catalyst to form a product mixture comprising the CBG or the CBG analog. In select embodiments, $R^1$ is $C_3H_7$, $C_5H_{11}$ or $C_7H_{15}$.

In an embodiment, the methods of the present disclosure further comprise a step of separating the CBG or the CBG analog from the product mixture obtained by the methods described herein.

In an embodiment, the methods of the present disclosure further comprise a step of purifying the CBG or the CBG analog provided by the methods described herein.

In another aspect, the present disclosure relates to a CBG or CBG analog composition obtained by the methods described herein.

In another aspect, the present disclosure relates to a high purity CBG or CBG analog obtained by the methods as described herein. In select embodiments, the high purity CBG or CBG analog has a purity of at least 90%, more particularly at least 95%, or even more particularly at least 99%.

In select embodiments of the present disclosure, the CBG analog is cannabigerovarin (CBGV).

In select embodiments of the present disclosure, the CBG analog is cannabigerophorol (CBGP).

In another aspect, the present disclosure relates to a method for preparing CBGA or a CBGA analog, the method comprising: combining CBG or a CBG analog with methylmagnesium carbonate (MMC) and a solvent to provide a product mixture comprising the CBGA or the CBGA analog.

In another aspect, the present disclosure relates to a method for preparing CBGA or a CBGA analog, the method comprising: providing a compound (II) of the following structure:

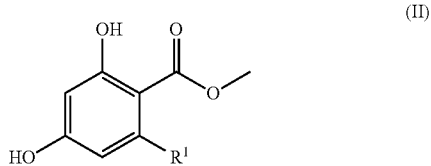

(II)

wherein $R^1$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}$ and $R^{2b}$ are each independently hydrogen or $C_1$-$C_6$ alkyl; combining the compound (II) with geraniol and a solvent to provide a reaction mixture; combining the reaction mixture with an acid catalyst to provide a first product mixture; and combining at least a portion of the first product mixture with one or more mild hydrolysis reagents to provide a second product mixture comprising the CBGA or CBGA analog. In select embodiments, $R^1$ is $C_3H_7$, $C_5H_{11}$ or $C_7H_{15}$.

In another aspect, the present disclosure relates to a CBGA or CBGA analog composition obtained by the methods as described herein.

In another aspect, the present disclosure relates to a high purity CBGA or CBG analog obtained by the methods as described herein. In select embodiments, the high purity CBGA or CBGA analog has a purity of at least 90%.

Other aspects and features of the present disclosure will become apparent to those ordinarily skilled in the art upon review of the following description of specific embodiments.

BRIEF DESCRIPTION OF THE DRAWINGS

FIG. 5A shows a chromatogram of a product mixture comprising about 20% CBG provided by the methods disclosed herein. FIG. 5B shows a chromatogram of the distillate comprising about 40% CBG and obtained from the product mixture. FIGS. 5C and 5D show chromatograms of recovered geraniol and olivetol, respectively. FIG. 5E shows a chromatogram of CBG crystals after separation from the product mixture and crystallization.

DETAILED DESCRIPTION

Figure 1:
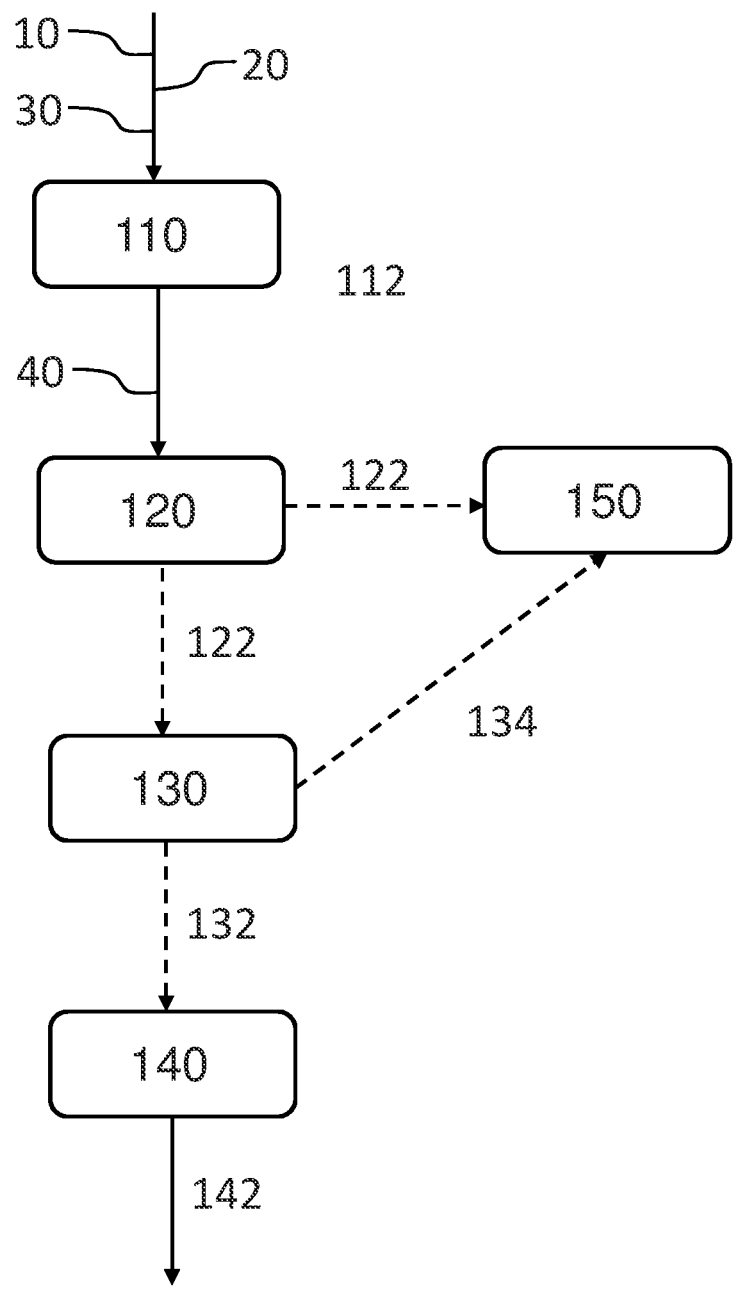
FIG. 1 shows a schematic of a method in accordance with the present disclosure where CBG or a CBG analog is prepared and can be isolated in high purity.

An important aspect of the cannabis industry is having cost-effective access to sufficient quantities of cannabinoids, including those less abundant in cannabis plant material.

In many instances, it may be desirable to isolate large quantities of cannabinoids that are present in low quantities in cannabis plant material or cannabis extracts. Further, it may be desirable to prepare cannabinoid analogs, as some cannabinoid homologs have been shown to improve binding affinity to CB1 receptors.

The present disclosure relates to methods for synthesizing cannabigerol (CBG), cannabigerolic acid (CBGA), and analogs thereof. The methods disclosed herein may be used to provide compositions enriched in CBG, CBGA, or analogs thereof, which may then be further purified to yield high purity compositions or high purity cannabinoids (e.g. CBG, CBGA, or analogs thereof).

An advantageous aspect of the synthetic methods provided herein is that CBG and CBGA can be prepared in large quantities that would otherwise not be accessible from extraction of cannabis plant material. A further advantage of the present disclosure is the provision of CBG and CBGA analogs, which may not be naturally occurring. Without being bound by any particular theory, analogs of CBG or CBGA may be of interest for their properties with respect to binding affinities to cannabinoid receptors (e.g. CB1 and/or CB2).

As used herein, the term "analog" is intended to refer to compounds that differ at the meta-position with respect to the hydroxyl groups of the resorcinol moiety. In select embodiments of the present disclosure, the substituent may be any of the $R^1$ substituents defined herein. In the context of the present disclosure, analogs include homologs. The term "homolog" as used herein refers to a group or series of compounds that differ only with respect to the number of repeating units in the alkyl chain on the resorcinol moiety located at the meta-position with respect to the hydroxyl groups. More specifically, homologs of the present disclosure include alkyl chains on the resorcinol moiety of the formula —$(CH_2)_{0-11}CH_3$ with the repeating unit in the alkyl chain being the methylene (—$CH_2$—) unit. For example, CBG has a five-carbon alkyl chain length whereas the homologs cannabigerovarin (CBGV; sometimes also referred to as cannabigerovarin) and cannabigerophorol (CBGP) have three-carbon and seven-carbon alkyl chain lengths, respectively. The term homolog is not limited to homologs of naturally occurring cannabinoids and includes homologs of semi-synthetic and cannabinoid derivatives.

As used herein, the term "cannabinoid" refers to a chemical compound belonging to a class of secondary compounds commonly found in plants of genus cannabis, but also encompasses synthetic and semi-synthetic cannabinoids and any enantiomers thereof.

In select embodiments of the present disclosure, the cannabinoid is a compound found in a plant, e.g., a plant of genus cannabis, and is sometimes referred to as a phytocannabinoid. In select embodiments of the present disclosure, the cannabinoid is a compound found in a mammal, sometimes called an endocannabinoid. In select embodiments of the present disclosure, the cannabinoid is made in a laboratory setting, sometimes called a synthetic cannabinoid. In select embodiments of the present disclosure, the cannabinoid is derived or obtained from a natural source (e.g. plant) but is subsequently modified or derivatized in one or more different ways in a laboratory setting, sometimes called a semi-synthetic cannabinoid.

A notable cannabinoid of the phytocannabinoids is tetrahydrocannabinol (THC), the primary psychoactive compound in cannabis. Cannabidiol (CBD) is another cannabinoid that is a major constituent of the phytocannabinoids. There are at least 113 different cannabinoids isolated from cannabis, exhibiting varied effects.

Synthetic cannabinoids and semi-synthetic cannabinoids encompass a variety of distinct chemical classes, for example and without limitation: the classical cannabinoids structurally related to THC, the non-classical cannabinoids (cannabimimetics).

In many cases, a cannabinoid can be identified because its chemical name will include the text string "*cannabi*". However, there are a number of cannabinoids that do not use this nomenclature, such as for example those described herein.

Within the context of this disclosure, where reference is made to a particular cannabinoid, each of the acid and/or decarboxylated forms are contemplated as both single molecules and mixtures. As well, any and all isomeric, enantiomeric, or optically active derivatives are also encompassed. In particular, where appropriate, reference to a particular cannabinoid incudes both the "A Form" and the "B Form". For example, it is known that THCA has two isomers, THCA-A in which the carboxylic acid group is in the 1 position between the hydroxyl group and the carbon chain (A Form) and THCA-B in which the carboxylic acid group is in the 3 position following the carbon chain (B Form).

The present disclosure relates specifically to the cannabinoids CBG, CBGA and analogs thereof, each of CBG and CBGA having the following structural formula:

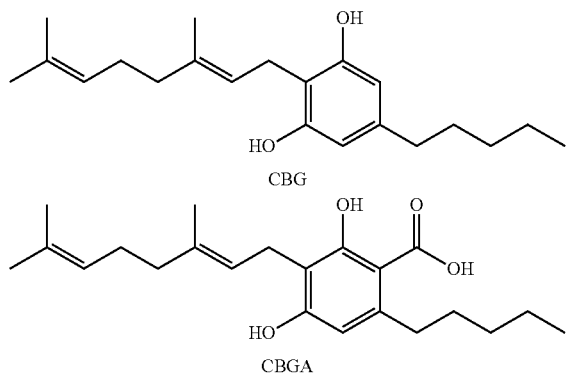

CBG

CBGA

In one aspect, the present disclosure provides a method for preparing CBG or a CBG analog, the method comprising: providing a compound (I) of the following structure:

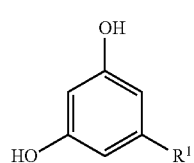

(I)

wherein $R^1$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}$ and $R^{2b}$ are each independently hydrogen or $C_1$-$C_6$ alkyl; combining the compound (I) with geraniol and a solvent to form a reaction mixture; and combining the reaction mixture with an acid catalyst to form a product mixture comprising the CBG or the CBG analog.

As used herein, the term "alkyl" refers to a saturated hydrocarbon having a designated number of carbon atoms, such as 1 to 12 carbons (i.e., inclusive of 1 and 12), 1 to 8 carbons, 1 to 6 carbons, 1 to 3 carbons, or 1, 2, 3, 4, 5, 6, 7 or 8 carbons. The alkyl group may be straight or branched and depending on context, may be a monovalent radical or a divalent radical (i.e., an alkylene group). For example, the moiety "—($C_1$-$C_6$ alkyl)-O—" signifies connection of an oxygen through an alkylene bridge having from 1 to 6 carbons. Examples of "alkyl" include, for example, methyl, ethyl, propyl, isopropyl, butyl, pentyl, hexyl, and heptyl.

The term "alkenyl" as used herein, refers to an unsaturated hydrocarbon containing from 2 to 12 carbons (i.e., inclusive of 2 and 12), 2 to 8 carbons, 2 to 6 carbons, or 2, 3, 4, 5 or 6, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, and 2-methyl-1-heptenyl.

The term "alkynyl" as used herein, refers to an unsaturated hydrocarbon containing from 2 to 12 carbons (i.e., inclusive of 2 and 12), 2 to 8 carbons, 2 to 6 carbons, or 2, 3, 4, 5 or 6 unless otherwise specified, and containing at least one carbon-carbon triple bond. Alkynyl group may be straight or branched and depending on context, may be a monovalent radical or a divalent radical (i.e., an alkynylene group). Representative examples of alkynyl include, but are not limited to, acetylenyl, 1-propynyl, 2-propynyl, and 3-butynyl.

The term "aryl" represents an aromatic ring system having a single ring (e.g., phenyl) which is optionally fused to other aromatic hydrocarbon rings or non-aromatic hydrocarbon or heterocycle rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, and dihydronaphthyl. "Aryl" also includes ring systems having a first carbocyclic, aromatic ring fused to a nonaromatic heterocycle, for example, 1H-2,3-dihydrobenzofuranyl. The aryl groups herein can be substituted in one or more substitutable positions, or not.

The term "heteroaryl" refers to an aromatic ring system containing at least one aromatic heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic rings, for example, cycloalkyl or heterocycloalkyl rings, wherein the cycloalkyl and heterocycloalkyl rings are described herein. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, and pyrrolyl. The heteroaryl groups herein may be substituted in one or more substitutable positions, or not.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, piperazinyl, pyrrolidinyl, azepanyl, azetidinyl, pyrrolinyl, tetrahydropyranyl, piperidinyl, tetrahydrofuranyl, 3,4-dihydroisoquinolin-2(1H)-yl, γ-butyrolactonyl (i.e., an oxo-substituted tetrahydrofuranyl), γ-butryolactamyl (i.e., an oxo-substituted pyrrolidine), azetidinyl, thiomorpholinyl, imidazolidonyl, isoindolindionyl, piperazinonyl. The heterocycloalkyl groups herein may be substituted in one or more substitutable positions, or not.

The methods herein for preparing CBG or a CBG analog comprise combining the compound (I) with geraniol and a solvent to form a reaction mixture.

As used herein, the term "solvent" is meant to refer to a substance that dissolves a solute (e.g. one or more reagents). In select embodiments, the solvent is a liquid. In an embodiment, the solvent is a hydrocarbon or halogenated hydrocarbon solvent. In exemplary embodiments of the present disclosure, the solvent is chloroform, heptane, tert-butylmethyl ether (TBME), diethyl ether, dichloromethane, dichloroethane, trifluorotoluene, hexane, cyclohexane, pentane, or any combination thereof. In a particular embodiment, the solvent is chloroform.

Geraniol is a monoterpenoid and an alcohol that is soluble in common organic solvents and consists of the following form:

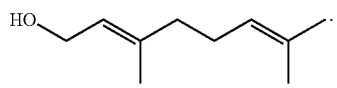

The combining of the compound (I) with geraniol and a solvent may be done in any order to form the reaction mixture. For example, the combining may comprise adding the compound (I) to the geraniol and adding the solvent thereto. In other embodiments, the compound (I) and the geraniol may each be in the solvent prior to combining. The combining may be done by any suitable means such that the compound (I) and geraniol are brought together. In an embodiment, the combining involves mixing such as, but not limited to, stirring in a reaction flask or vessel.

In select embodiments, the combining of the compound (I) with geraniol and a solvent comprises a compound (I):geraniol molar ratio of between about 10:1 and about 1:10, more particularly between about 5:1 and about 1:5, and more particularly still between about 1:1.5 and about 1:3.5.

As the skilled person will appreciate, the term "molar ratio" refers to the proportion of the reagents on a molar basis. In an embodiment, the compound (I):geraniol molar ratio is between about 1:1.5 to about 1:2. In an embodiment, the compound (I):geraniol molar ratio is about 1:1.5, about 1:1.6, about 1:1.7, about 1:1.8, about 1:1.9, about 1:2.0 about 1:2.1, about 1:2.2, about 1:2.3, about 1:2.4, about 1:2.5, about 1:2.6 about 1:2.7 about 1:2.8, about 1:2.9, about 1:3.0, about 1:3.1, about 1:3.2, about 1:3.3, about 1:3.4, or about 1:3.5. In a particular embodiment, the compound (I):geraniol molar ratio is about 1:1.7.

The methods herein for preparing CBG or a CBG analog further comprise combining the reaction mixture above with an acid catalyst under a set of reaction conditions to form a product mixture comprising the CBG or the CBG analog.

As used herein, the term "acid catalyst" is intended to refer to an acid that increases the rate of chemical reaction without itself undergoing any change. In select embodiments of the present disclosure, the acid catalyst is p-toluenesulfonic acid monohydrate, camphorsulfonic acid, acidic alumina, montmorillonite K10, BF$_3$·Et$_2$O, iron (III) perchlorate hydrate, or a combination thereof.

In a particular embodiment, the acid catalyst is p-Toluenesulfonic acid monohydrate, an organic compound of the following form:

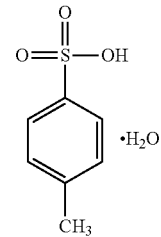

In another particular embodiment, the acid catalyst is camphorsulfonic acid, an organosulfur compound of the following form:

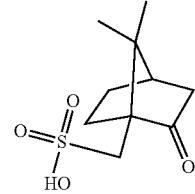

Both p-toluenesulfonic acid monohydrate and camphorsulfonic acid are soluble in water, alcohols, and other organic solvents. Without being bound by any particular theory, the acid catalyst may promote a reaction between the compound (I) and geraniol under the reaction conditions described herein to provide CBG or a CBG analog.

The combining may be done by any suitable means such that the reaction mixture and the acid catalyst are brought together. In an embodiment, the combining is by mixing. In select embodiments, the acid catalyst is added (e.g. dropwise) to the reaction mixture. Alternatively, the reaction mixture may be added to the acid catalyst. In select embodiments, the acid catalyst may be in a solvent, such as for example the solvents described herein.

In select embodiments of the present disclosure, the acid catalyst may be used in an amount of between about 0.001 and about 10 molar equivalents with respect to the amount of the compound (I), more particularly between about 0.01 and about 1.0 molar equivalents with respect to the amount of the compound (I), and more particularly still between about 0.01 and about 0.5 molar equivalents with respect to the amount of the compound (I). In an embodiment, the acid catalyst may be used in an amount of between about 0.01 and about 0.1 molar equivalents with respect to the amount of the compound (I). In an embodiment, the acid catalyst is in an amount of 0.01, 0.02, 0.03, 0.04, 0.05, 0.06, 0.07, 0.08, 0.09, or 0.1 molar equivalents with respect to the compound (I).

The reaction mixture and the acid catalyst are combined under a set of reaction conditions to form a product mixture comprising the CBG or the CBG analog. As used herein, the term "under a set of reaction conditions" is intended to refer to conditions such as temperature, pressure, and time used in the methods of the present disclosure. As the skilled person will appreciate, each of these variables may be dependent upon one or more of the others, such that changes to one may necessitate changes to the others.

In an embodiment of the methods herein, the pressure is atmospheric pressure. In other embodiments, the pressure is a pressure below atmospheric pressure also referred to as "reduced pressure". In an embodiment, the reaction pressure is between about 0.1 mbar and 1000 mbar, more particularly between about 0.1 mbar and 500 mbar, between about 0.1 mbar and 100 mbar, or between about 0.5 mbar and 10 mbar.

In select embodiments, combining the reaction mixture with an acid catalyst under a set of reaction conditions comprises stirring at a particular temperature for a particular time. In an embodiment, the temperature is between about 5° C. and about 35° C., more particularly between about 10° C. and about 30° C., and more particularly still between about 15° C. and about 30° C. In select embodiments, the temperature is about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., or about 30° C. In a particular embodiment, the temperature is room temperature, conventionally understood to be about 20° C.

In an embodiment, the time is between about 30 minutes and about 72 hours, more particularly between about 6 hours and about 60 hours, more particularly still between about 12 hours and about 48 hours. In a more particular embodiment, the time is between about 14 hours and about 24 hours. In select embodiments, the time is about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 25 hours. In a particular embodiment, the time is about 14 hours.

In a particular embodiment, the combining of the reaction mixture and the acid catalyst is performed at a temperature between about 15° C. and about 30° C. and at a time between about 14 hours and about 48 hours, more particularly at about 20° C. and for about 14 hours.

The methods disclosed herein provide a product mixture that comprises CBG or a CBG analog. As used herein, the term "product mixture" is intended to refer to a mixture that comprises CBG or the CBG analog and at least one other component that is produced by the methods disclosed herein. In select embodiments, the at least one other component may be one or more unreacted reagents. For example, the at least one other component may be the acid catalyst and/or may be a reaction by-product.

In select embodiments of the present disclosure, the product mixture comprises the CBG or the CBG analog in an amount of between about 1% w/w and about 99.99% w/w, or more particularly between about 5% w/w and about 95%, about 10% w/w and about 75% w/w, between about 10% w/w and about 50% w/w, or between about 15% w/w and about 40% w/w. In an embodiment, the product mixture comprises between about 1% w/w and about 65% w/w, more particularly between about 10% w/w and about 35% w/w, or between about 15% w/w and about 25% w/w. In an embodiment, the product mixture comprises between about 5% w/w and about 25% w/w. In an embodiment, the product mixture comprises about 1.0%, about 2.5%, about 5.0%, about 7.5%, about 10.0%, about 12.5%, about 15.0%, about 17.5%, about 20.0%, about 22.5%, about 25%, about 27.5%, about 30%, about 32.5%, about 35%, about 37.5%, about 40%, about 42.5%, about 45%, about 47.5%, about 50%, about 52.5%, about 55%, about 57.5%, about 60%, about 65%, about 70%, about 75%, about 80%, about 85%, about 90%, about 95%, or greater w/w CBG or CBG analog. In other embodiments, the product mixture comprises the CBG or the CBG analog in an amount of at least about 15% by weight, at least 20% by weight, or more. In a particular embodiment, the product mixture comprises the CBG or the CBG analog in an amount of at least about 20% by weight. By "at least about X % by weight" it is meant that of the total weight of the product mixture provided by the method disclosed herein, at least that "X" percentage is attributed to the weight of the CBG or CBG analog.

In select embodiments herein, $R^1$ is $C_5H_{11}$ and the product mixture comprises CBG. In other embodiments, $R^1$ is $C_3H_7$ and the product mixture comprises cannabigerovarin (CBGV). In other embodiments still, $R^1$ is $C_7H_{15}$ and the product mixture comprises cannabigerophorol (CBGP).

The methods for preparing CBG or a CBG analog disclosed herein may further comprise a step of separating the CBG or the CBG analog from the product mixture. The separating may be by any suitable method or means. In select embodiments, the separating comprises one or both of a chromatography step and a distillation step.

Separation by chromatography may comprise, for example, a normal phase flash chromatography with a solvent system comprising heptane and one of tert-butyl methyl ether (TBME) or acetone. Flash chromatography is a form of chromatography that uses low to medium pressures to advance a solution through a chromatography column. The skilled person will appreciate that gravity flow or other forms of chromatography may also be used for the separating.

Separation by distillation may comprise, for example, a fractional distillation under reduced pressure. Fractional distillation separates a mixture into components based on differences in vaporization points. In select embodiments of the present disclosure, the distillation conditions may comprise about 0.2 mbar at a temperature of between about 52° C. and about 58° C. to distill unreacted geraniol; about 0.45 mbar at a temperature of between about 140° C. and about 150° C. to distill unreacted olivetol; and about 0.45 mbar at a temperature of between about 160° C. and about 180° C. to distill CBG or CBG analog. The skilled person will appreciate that other forms of distillation and other conditions may also be used to separate the CBG or CBG analog from the product mixture.

The methods herein for preparing CBG or a CBG analog may further comprise a step of purifying the CBG or CBG analog. In select embodiments, the purifying is by crystallization. As the skilled person will appreciate, crystallization is a process by which atoms or molecules arrange in a highly organized structure and precipitate out of a solution. Generally speaking, crystallization occurs from a saturated and/or cooled solution comprising the compound of interest. In select embodiments of the methods herein, the crystallization is in heptane. For example, the product mixture may be dissolved in heptane and cooled until at least some of the CBG or the CBG analog precipitates.

The methods for preparing CBG or a CBG analog may further comprise a step of recovering at least a portion of unreacted compound (I), at least a portion of unreacted geraniol, or both. As used herein, the term "recovering" is intended to refer to a process or means of obtaining a material in its original form after it has been used. Non-limiting examples of recovering at least a portion of the unreacted compound (I) are by distillation or chromatography.

The methods disclosed herein are suitable for preparing a composition comprising CBG or a CBG analog. In an embodiment, the CBG or CBG analog composition is the product mixture as described herein. In other embodiments, the CBG or CBG analog composition is a resultant composition prepared by subsequent separation or purification steps. In other embodiments, the CBG or CBG analog composition may be any of these compositions having additional components added thereto, such as an acceptable carrier, excipient, diluent or other additive, for example for pharmaceutical or recreational use of the CBG or CBG analog composition.

The present disclosure also provides a high purity CBG or CBG analog obtained by the methods herein. In an embodiment, the high purity CBG or CBG analog is obtained by utilizing the separating and/or purifying steps as described herein. As used herein, the term "high purity" is intended to refer to the extent to which the CBG or CBG analog, or the CBGA or CBGA analog described below, is free from other components, also referred to as impurities. In an embodiment of the present disclosure, the high purity CBG or CBG analog has a purity of at least 75%, and more particularly at least 90%. In an embodiment, the high purity CBG or CBG analog has a purity of at least 75%, at least 77.5%, at least 80%, at least 82.5%, at least 85%, at least 87.5%, at least 90%, at least 92.5%, at least 95%, at least 97.5%, or greater. In select embodiments, the high purity CBG or CBG analog has a purity of at least 95%. In further select embodiments, the high purity CBG or CBG analog has a purity of at least 99%. Crystallization may provide pure CBG or CBG analogs.

In another aspect, the present disclosure provides a method for preparing CBGA or a CBGA analog, the method comprising: combining CBG or a CBG analog with methylmagnesium carbonate (MMC) and a solvent to provide a product mixture comprising the CBGA or the CBGA analog.

In select embodiments of the present disclosure, the CBG is a CBG distillate, a CBG isolate, a semi-synthetic CBG, a synthetic CBG or any combination thereof. As used herein, the term "CBG distillate" is used to refer to a form of CBG oil produced by a distillation process, such as distillation of a cannabis resin. As used herein, the term "CBG isolate" is used to refer to CBG isolated in pure form, such as a crystalline solid or powder. In select embodiments, the synthetic CBG or CBG analog is provided by the methods disclosed herein for preparing CBG or a CBG analog.

The CBG or CBG analog are combined with MMC under a set of reaction conditions to form a product mixture comprising the CBGA or the CBGA analog. In select embodiments, the set of reaction conditions comprises stirring at a particular temperature for a particular time under an inert atmosphere. As used herein, the term "inert atmosphere" is intended to refer to a nonreactive gas atmosphere, such as nitrogen, argon, or helium. In select embodiments of the methods herein, the inert atmosphere comprises argon, nitrogen, or a combination thereof. In an embodiment, the temperature is between about 40° C. and about 180° C., more particularly between about 60° C. and about 160° C., more particularly still between about 100° C. and about 140° C. In an embodiment, the temperature is about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., or about 140° C. In an embodiment, the time is between about 30 minutes and about 72 hours, more particularly between 1 hour and 48 hours, and more particularly still between 2 hours and 24 hours. In an embodiment, the time is about 1 hour, about 2 hours, about 3 hours, about 4 hours, about 5 hours, about 6 hours, about 7 hours, about 8 hours, about 9 hours, about 10 hours, about 11 hours, about 12 hours, or longer. In select embodiments, the temperature is between about 60° C. and about 160° C. and the time is between about 0.5 hours and about 48 hours. In a particular embodiment, the temperature is about 125° C. and the time is about 2.5 hours.

As described elsewhere herein, the term "solvent" refers to a substance that dissolves a solute (e.g. one or more reagents). In select embodiments of the methods for preparing CBGA or a CBGA analog, the solvent is dimethylformamide. In other embodiments, the solvent may be dimethyl sulfoxide (DMSO), N,N'-dimethylpropyleneurea (DMPU), dimethyl acetamide, tetrahydrofuran (THF), or propylene carbonate.

The method for preparing CBGA or a CBGA analog may further comprises a step of crystallization. In select embodiments of the methods herein, the step of crystallization comprises combining the CBGA or CBGA analog with a solvent mixture. The solvent mixture may comprise, for example and without limitation, acetone and heptane.

In a further aspect, the present disclosure provides a method for preparing CBGA or a CBGA homolog, where the method comprises: providing a compound (II) of the following structure:

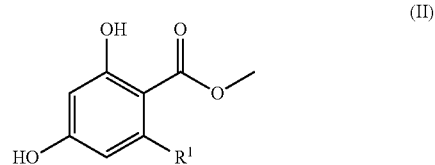

(II)

wherein $R^1$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl$)$, $(C_0$-$C_4$ alkyl$)$-$NR^{2a}R^{2b}$, $(C_0$-$C_4$ alkyl$)$-aryl, $(C_0$-$C_4$ alkyl$)$-heteroaryl, $(C_0$-$C_4$ alkyl$)$-cycloalkyl, or $(C_0$-$C_4$ alkyl$)$-heterocycloalkyl, wherein $R^{2a}$ and $R^{2b}$ are each independently hydrogen or $C_1$-$C_6$ alkyl; combining the compound (II) with geraniol and a solvent to provide a reaction mixture; combining the reaction mixture with an acid catalyst to provide a first product mixture; and combining at least a portion of the first product mixture with one or more mild hydrolysis reagents to provide a second product mixture comprising the CBGA or CBGA analog.

As used herein, the term "mild hydrolysis reagent" is intended to refer to a reagent that promotes the conversion of an ester functional group on a compound to a carboxylic acid functionality, without reacting with other parts of the compound.

In embodiments of the methods herein for preparing CBGA or a CBGA analog, the combining the compound (II) with geraniol and a solvent to provide a reaction mixture may be performed as described herein in relation to combining the compound (I) with geraniol and a solvent to prepare CBG or a CBG analog.

In select embodiments of the methods herein, the combining of the compound (II) with geraniol and a solvent comprises a compound (II):geraniol molar ratio of between about 10:1 and about 1:10, more particularly between about 5:1 and about 1:5, and more particularly still between about 1:1.5 and about 1:3.5. In an embodiment, the a compound (II):geraniol molar ratio is between about 1:1.5 to about 1:2. In an embodiment, the compound (II):geraniol molar ratio is about 1:1.5, about 1:1.6, about 1:1.7, about 1:1.8, about 1:1.9, about 1:2.0 about 1:2.1, about 1:2.2, about 1:2.3, about 1:2.4, about 1:2.5, about 1:2.6 about 1:2.7 about 1:2.8, about 1:2.9, about 1:3.0, about 1:3.1, about 1:3.2, about 1:3.3, about 1:3.4, or about 1:3.5. In a particular embodiment, the compound (II):geraniol molar ratio is about 1:1.7.

The step of forming the reaction mixture comprises combining the compound (II) with geraniol and a solvent. In select embodiments of the methods for preparing CBGA or a CBGA analog, the solvent is chloroform, heptane, TBME, or a combination thereof. In a particular embodiment, the solvent is chloroform.

The methods herein for preparing CBGA or a CBGA analog further comprise combining the reaction mixture above with an acid catalyst under a set of reaction conditions to form a product mixture comprising the CBGA or the CBGA analog. The combining of the reaction mixture with the acid catalyst may be by any of the means disclosed elsewhere herein in relation to the methods for preparing CBG or a CBG analog. In an embodiment, the acid catalyst is p-toluenesulfonic acid monohydrate, camphorsulfonic acid, or a combination thereof. In a particular embodiment, the acid catalyst is p-toluenesulfonic acid monohydrate. In another particular embodiment, the acid catalyst is camphorsulfonic acid.

In select embodiments of the present disclosure, the acid catalyst may be used in an amount of between about 0.001 and about 10 molar equivalents with respect to the amount of the compound (I), more particularly between about 0.01 and about 1.0 molar equivalents with respect to the amount of the compound (I), and more particularly still between about 0.01 and about 0.5 molar equivalents with respect to the compound (II). In an embodiment, the acid catalyst may be used in an amount of between about 0.01 and about 0.1 molar equivalents with respect to the compound (II). In an embodiment, the acid catalyst is in an amount of 0.01, 0.02, 0.03, 0.04, 0.05, 0.06, 0.07, 0.08, 0.09, or 0.1 molar equivalents with respect to the compound (II).

The reaction mixture and the acid catalyst are combined under a first set of reaction conditions to form a first product mixture. The first set of reaction conditions comprise a temperature, pressure and time. As the skilled person will appreciate, each of these variables may be dependent upon one or more of the others, such that changes to one may necessitate changes to the others.

In an embodiment of the methods herein for preparing CBGA or a CBGA analog, the pressure is atmospheric pressure. In other embodiments, the pressure is a pressure below atmospheric pressure also referred to as "reduced pressure". In an embodiment, the reaction pressure is between about 0.1 mbar and 1000 mbar, more particularly between about 0.1 mbar and 500 mbar, between about 0.1 mbar and 100 mbar, or between about 0.5 mbar and 10 mbar.

In select embodiments, combining the reaction mixture with an acid catalyst under a first set of reaction conditions comprises stirring at a particular temperature for a particular time. In an embodiment, the temperature is between about 5° C. and about 35° C., more particularly between about 10° C. and about 30° C., and more particularly still between about 15° C. and about 30° C. In select embodiments, the temperature is about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., or about 30° C. In a particular embodiment, the temperature is room temperature, conventionally understood to be about 20° C.

The time may be any suitable for the reaction to occur. In an embodiment, the time is between about 30 minutes and about 72 hours, more particularly between about 6 hours and about 60 hours, more particularly still between about 12 hours and about 48 hours. In a more particular embodiment, the time is between about 10 hours, about 11 hours, about 12 hours, about 13 hours, about 14 hours and about 24 hours. In select embodiments, the time is about 14 hours, about 15 hours, about 16 hours, about 17 hours, about 18 hours, about 19 hours, about 20 hours, about 21 hours, about 22 hours, about 23 hours, or about 25 hours. In a particular embodiment, the time is about 14 hours.

In select embodiments of the methods for preparing CBGA or a CBGA analog, the temperature is between about 15° C. and about 30° C. and the time is between about 12 hours and about 48 hours, more particularly at about 20° C. and for about 14 hours.

The methods herein for preparing CBGA or a CBGA analog further comprise a step of combining at least a portion of the first product mixture with one or more mild hydrolysis reagents under a second set of reaction conditions to provide a second product mixture comprising the CBGA or CBGA analog. In select embodiments, this step comprises (a) combining the first product mixture with thiophenol and cesium carbonate, and (b) adding dilute hydrochloric acid. The skilled person will appreciate that other mild hydrolysis reagents may be used to convert the ester moiety to a carboxylic acid.

The first product mixture and the one or more mild hydrolysis reagents are combined under a second set of reaction conditions. In select embodiments, the second set of reaction conditions comprises stirring at a particular temperature for a particular time. In an embodiment, the temperature is between about 40° C. and about 180° C., more particularly between about 60° C. and about 160° C., more particularly still between about 100° C. and about 140° C. In an embodiment, the temperature is about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., or about 140° C. In an embodiment, the time is between about 30 minutes and about 72 hours, more particularly between 1 hour and 48 hours, and more particularly still between 2 hours and 24 hours. In an embodiment, the time is about 1 hour, about 2 hours, about 3 hours, about 4 hours, about 5 hours, about 6 hours, about 7 hours, about 8 hours, about 9 hours, about 10 hours, about 11 hours, about 12 hours, or longer. In a particular embodiment, the temperature is between about 60° C. and 160° C. and the time is between about 0.5 and 48 hours.

The methods herein for preparing CBGA or a CBGA analog may further comprise separating the CBGA or the CBGA analog from the second product mixture. In select embodiments, the separating comprises one or both of a chromatography step and a fractional distillation step as described elsewhere herein for the separation of CBG or CBGA analogs.

The methods herein for preparing CBGA or a CBGA analog may further comprise purifying the CBGA or the CBGA analog. In select embodiments, the purifying is by crystallization as described elsewhere herein for the separation of CBG or CBGA analogs.

The methods for preparing CBGA or a CBGA analog may further comprise a step of recovering at least a portion of unreacted compound (II), at least a portion of unreacted geraniol, or both. As used herein, the term "recovering" is intended to refer to a process or means of obtaining a material in its original form after it has been used. In select embodiments, the step of recovering compound (II) is as described elsewhere herein for the recovery of compound (I).

The methods disclosed herein are suitable for preparing a composition comprising CBGA or a CBGA analog. In an embodiment, the CBGA or CBGA analog composition is the product mixture as described herein. In other embodiments, the CBGA or CBGA analog composition is a resultant composition from subsequent separation or purification steps. In other embodiments, the CBGA or CBGA analog composition may be any of these compositions having additional components added thereto, such as an acceptable carrier, excipient, diluent or other additive, for example for pharmaceutical or recreational use of the CBG or CBG analog composition.

The present disclosure also provides a high purity CBGA or CBGA analog obtained by the methods disclosed herein. In an embodiment, the high purity CBGA or CBGA analog is obtained by utilizing the separating and/or purifying steps as described herein. In select embodiments, the high purity CBGA or CBGA analog has a purity of at least 75%, and more particularly at least 90%. In an embodiment, the high purity CBGA or CBGA analog has a purity of at least 75%, at least 77.5%, at least 80%, at least 82.5%, at least 85%, at least 87.5%, at least 90%, at least 92.5%, at least 95%, at least 97.5%, or greater. In select embodiments, the high purity CBGA or CBGA analog has a purity of at least 95%. In further select embodiments, the high purity CBG or CBG analog has a purity of at least 99%. Crystallization may provide pure CBG or CBG analogs.

Embodiments of the present disclosure will now be described by reference to FIG. 1 to FIG. 3, which show representations of the methods for isolating CBG, CBGA and analogs thereof, according to the methods of the present disclosure.

FIG. 1 shows a flow diagram for a method 100 for preparing CBG or a CBG analog in accordance with the methods disclosed herein. The method 100 comprises the following steps: combing (110) a compound (I) 10 with geraniol 20 and a solvent 30 to form a reaction mixture 112; and combining (120) the reaction mixture 112 with an acid catalyst 40 to form a product mixture 122 comprising the CBG or the CBG analog. The method 100 may further comprise a step of separating (130) the CBG or CBG analog 132 from the product mixture 122. The method 100 may further comprise a step of purifying (140) the separated CBG or CBG analog 132 to provide a high purity CBG or CBG analog 142. The method 100 may further comprise a step 150 of recovering at least a portion of the compound (I) 10, at least a portion of the geraniol 20, or both. The recovering may be from the product mixture 122 or from the mixture 134 remaining after the separating step.

Figure 2:
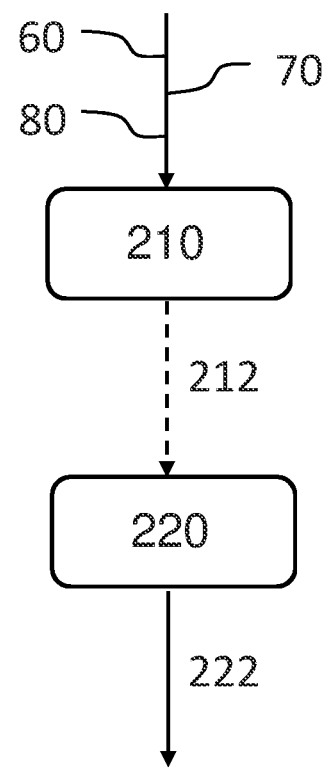
FIG. 2 shows a schematic of a method in accordance with the present disclosure where CBGA or a CBGA analog is prepared from CBG or a CBG analog and can be isolated in high purity.

FIG. 2 shows a flow diagram for a method 200 for preparing a CBGA or a CBGA analog in accordance with the methods of the present disclosure. The method 200 comprises combining (210) CBG or a CBG homolog 60 with methylmagnesium carbonate (MMC) 70 and a solvent 80 to provide a product mixture 212 comprising the CBGA or the CBGA homolog 222. The method may further comprise a step of purifying (220) the product mixture 212 to provide the CBG or CBG analog 222 in higher purity.

Figure 3:
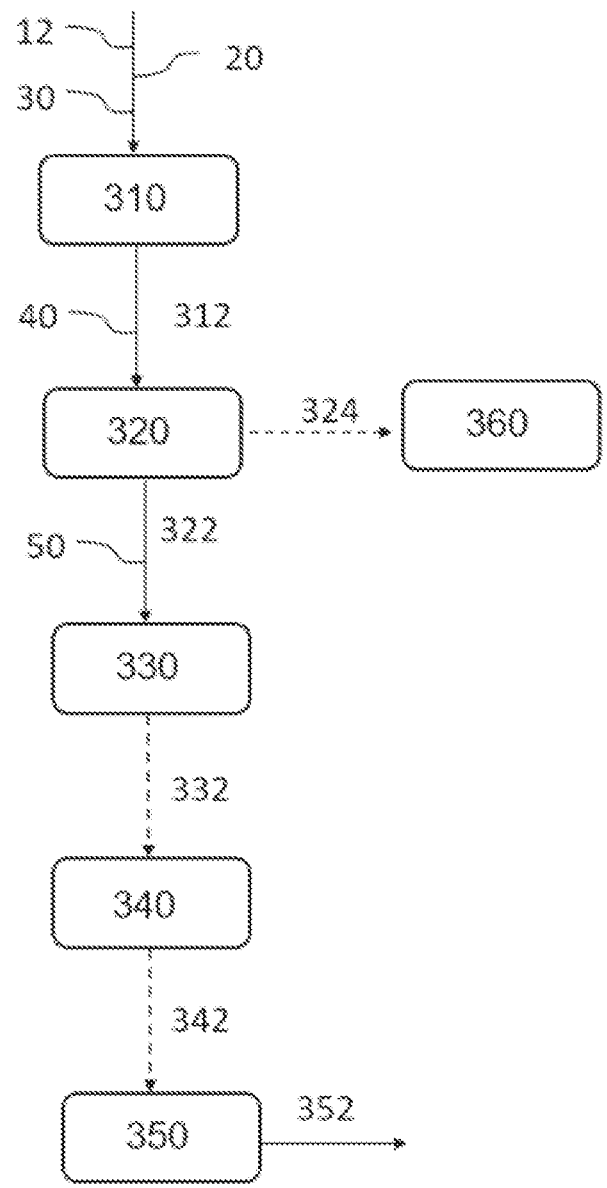
FIG. 3 shows a schematic of an alternate method of preparing CBGA or a CBGA analog in accordance with the present disclosure.

FIG. 3 shows a flow diagram for a method 300 for preparing CBGA or a CBGA analog in accordance with the methods of the present disclosure. The method 300 comprises the following steps: combining (310) a compound (II) 12 with geraniol 20 and a solvent 30 to form a reaction mixture 312; combining (320) the reaction mixture 312 with an acid catalyst 40 to form a first product mixture 322; and combining (330) at least a portion of the first product mixture 322 with one or more mild hydrolysis reagents 50 to provide a second product mixture 332 comprising the CBGA or the CBGA analog. The method 300 may further comprise a step of separating (340) the CBGA or CBGA analog from the product mixture 332. The method 300 may further comprise a step of purifying (350) the separated CB G or CB G analog 342 to provide a high purity CBG or CBG analog 352. The method 300 may further comprise a step 360 of recovering at least a portion of the compound (II) 12, at least a portion of the geraniol 20, or both.

EXAMPLES

Example 1

General reaction scheme for the synthesis of compositions comprising CBG:

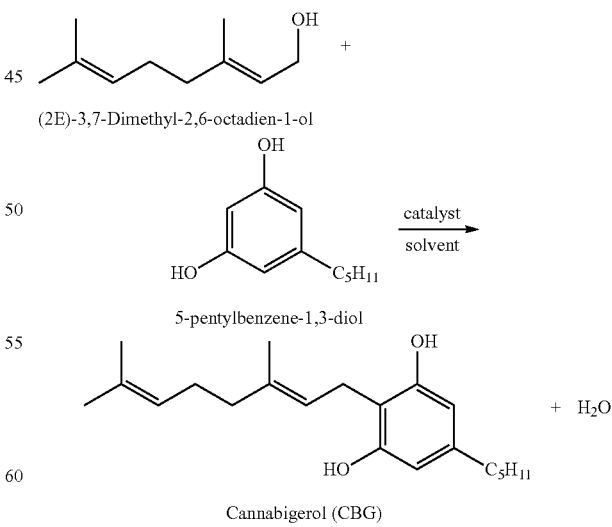

In a typical experiment, 5-pentylbenzene-1,3-diol (olivetol) and a molar excess of (2E)-3,7-dimethyl-2,6-octadien-1-ol (geraniol) were combined in a solvent. To this mixture was added an acidic catalyst. The reaction mixture was allowed to stir for a period of time at a temperature to produce a product mixture comprising CBG or a CBG analog.

Example 2

The general procedure from Example 1 was used to study the effects of geraniol equivalents, catalyst equivalents, catalyst, solvent, reaction temperature, and reaction time on CBG yield. The results from experiments are summarized in Tables 1 & 2.

TABLE 1

Preparation of Compositions Comprising CBG

| Olivetol (g, mmol) | Geraniol Equivalents | Catalyst Equivalents | Catalyst | Solvent | T (° C.) | t (hours) | Approximate CBG (w/w %) |
|---|---|---|---|---|---|---|---|
| 1, 5.55 | 1.7 | 0.01 | TsOH•$H_2$O | $CHCl_3$ | 20 | 14 | 20 |
| 1, 5.55 | 1.7 | 0.08 | TsOH•$H_2$O | $CHCl_3$ | 20 | 14 | 20 |
| 1, 5.55 | 1.7 | 0.01 | camphorsulfonic acid | $CHCl_3$ | 20 | 14 | 18 |
| 1, 5.55 | 1.7 | 0.1 | camphorsulfonic acid | $CHCl_3$ | 20 | 14 | 19 |
| 1, 5.55 | 2.6 | 0.01 | TsOH•$H_2$O | $CHCl_3$ | 20 | 14 | 15 |
| 1, 5.55 | 3.5 | 0.01 | TsOH•$H_2$O | $CHCl_3$ | 20 | 14 | 15 |
| 1, 5.55 | 1.7 | 0.01 | TsOH•$H_2$O | $CHCl_3$ | 50 | 14 | trace |
| 1, 5.55 | 1.7 | 0.01 | TsOH•$H_2$O | $CHCl_3$ | 60 | 14 | trace |
| 1, 5.55 | 1.7 | 0.01 | TsOH•$H_2$O | $CHCl_3$ | 20 | 38 | 18 |
| 1, 5.55 | 1.7 | 0.01 | TsOH•$H_2$O | Ethyl acetate | 20 | 14 | 0 |
| 1, 5.55 | 1.7 | 0.01 | TsOH•$H_2$O | Acetone | 20 | 14 | 0 |
| 1, 5.55 | 1.7 | 0.01 | TsOH•$H_2$O | Ethanol | 20 | 14 | 0 |
| 1, 5.55 | 1.7 | 0.01 | TsOH•$H_2$O | TBME | 20 | 14 | 10 |
| 1, 5.55 | 1.7 | 0.01 | TsOH•$H_2$O | Heptane | 20 | 14 | 8 |

TABLE 2

Preparation of Compositions Comprising CBG

| Olivetol (g) (1 eq.) | Geraniol Equivalents | Catalyst (g) | Catalyst | Solvent | T (° C.) | t (hours) | Approximate CBG (w/w %) |
|---|---|---|---|---|---|---|---|
| 1.000 | 1.2 | 1.0 g | $Al_2O_3$, acidic Brockman I | $CHCl_3$ | 66 | 24 | 8 |
| 0.252 | 1.2 | 0.252 g | $Al_2O_3$, acidic Brockman I | none | 85 | 24 | 19 |
| 0.252 | 1.2 | 0.252 g | $Al_2O_3$, acidic Brockman I | $CHCl_3$:PhMe 1:1 | 85 | 24 | 23 |
| 0.108 | 1.6 | 0.016 g/ 0.221 g | TsOH•$H_2$O/$Na_2SO_4$ | $CHCl_3$ | 85 | 24 | 29 |
| 0.108 | 1.6 | 0.016 | TsOH•$H_2$O | $CHCl_3$ | 85 | 24 | 35 |
| 0.204 | 1.7 | 0.1 | Fe($ClO_4$)$_3$ n$H_2$O | $CHCl_3$ | RT | 24 | 19 |
| 0.204 | 1.7 | 0.08 | $CF_3$COOH | $CHCl_3$ | RT | 24 | 1 |
| 0.204 | 1.7 | 0.1 | camphorsulfonic acid | $CHCl_3$ | RT | 24 | 26 |
| 0.204 | 1.7 | 0.20 mL/ 1.9 g | $BF_3$•$Et_2$O/$SiO_2$ | $CHCl_3$ | RT | 24 | 20 |
| 0.204 | 1.7 | 0.204 g | montmorillonite K10 | $CHCl_3$ | RT | 24 | 21 |

Example 3

Figure 4:
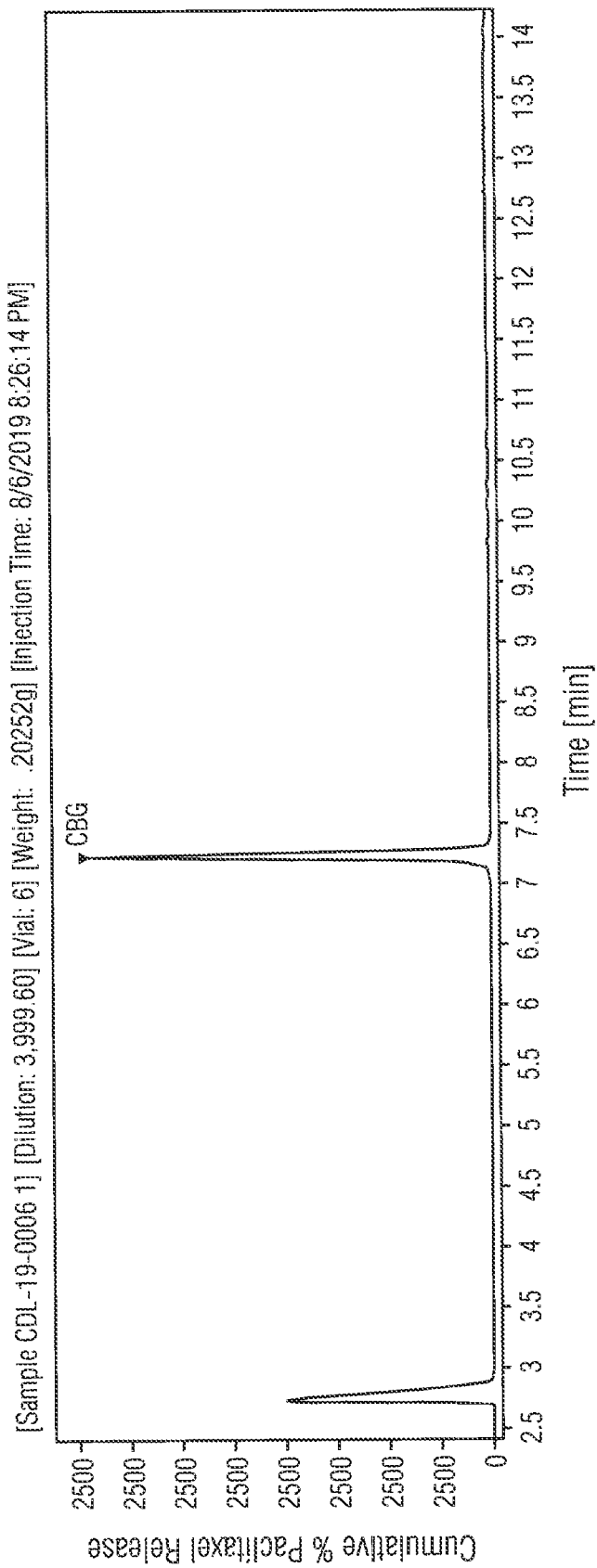
FIG. 4 shows a high performance liquid chromatography (HPLC) chromatogram of high purity CBG provided by the methods of the present disclosure.

Olivetol (1 g, 5.55 mmol) was combined with geraniol (1.45 g, 9.44 mmol) in chloroform. To the mixture was added p-toluenesulfonic acid monohydrate (0.055 mmol). The reaction mixture was stirred at room temperature for 14 hours. Normal phase flash chromatography with an acetone/heptane solvent system was performed to separate the CBG from the reaction mixture. High performance liquid chromatography (HPLC) demonstrated that the CBG was isolated in >97% purity (FIG. 4). The CBG was further purified by crystallization from heptane to isolate CBG as colourless crystals (25% yield).

Example 4

Figure 5A:
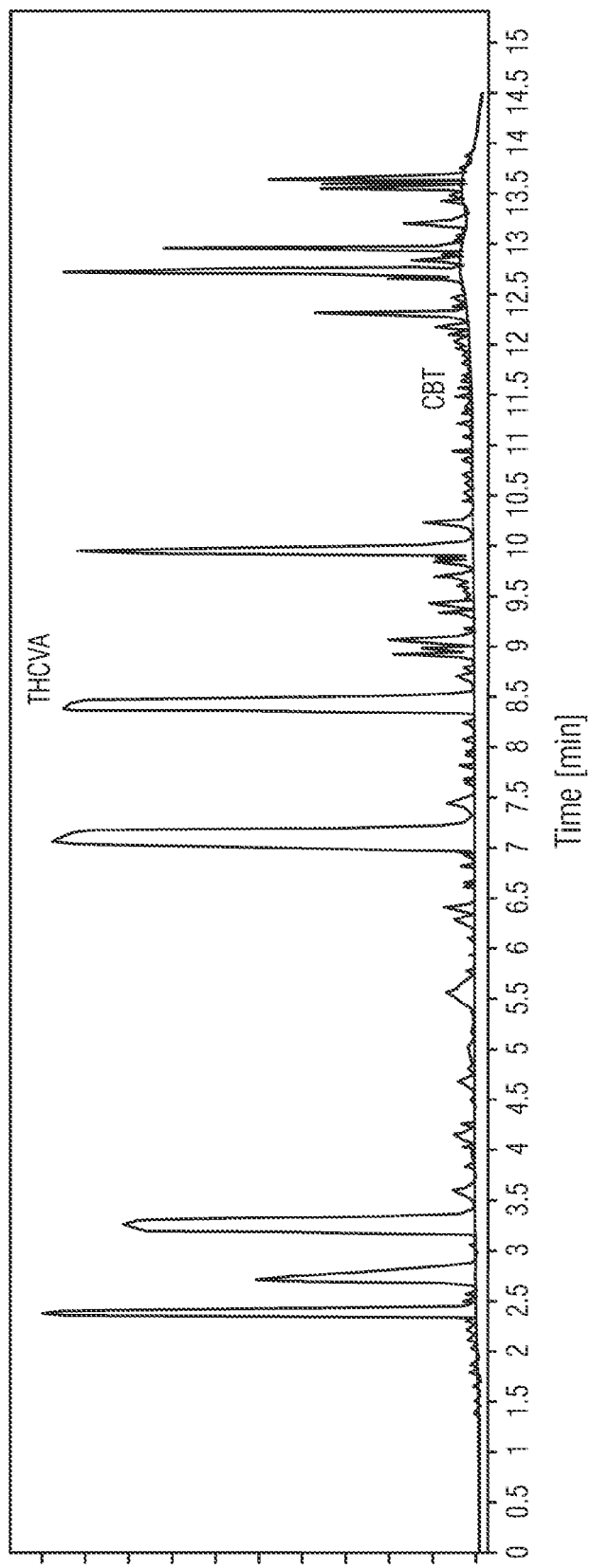
FIGS. 5A-5E show HPLC chromatograms of CBG prepared and purified by a method of the present disclosure and recovered reactants.
Figure 5B:
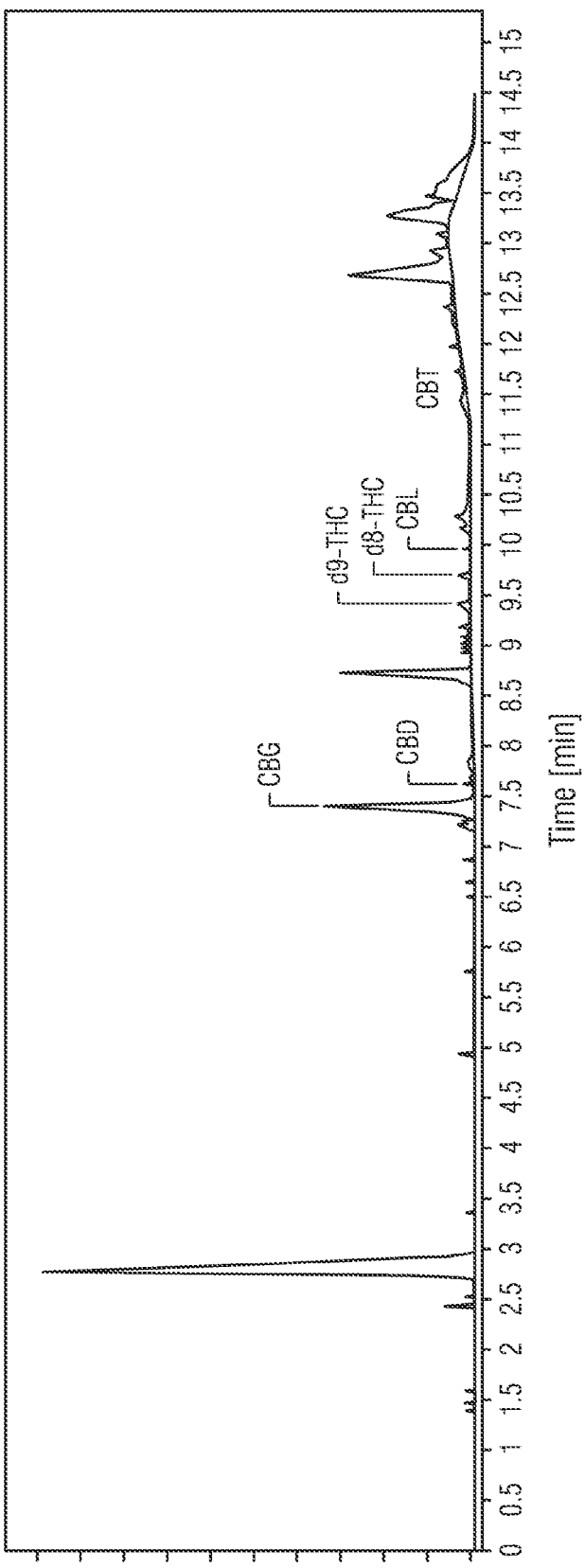
Figure 5C:
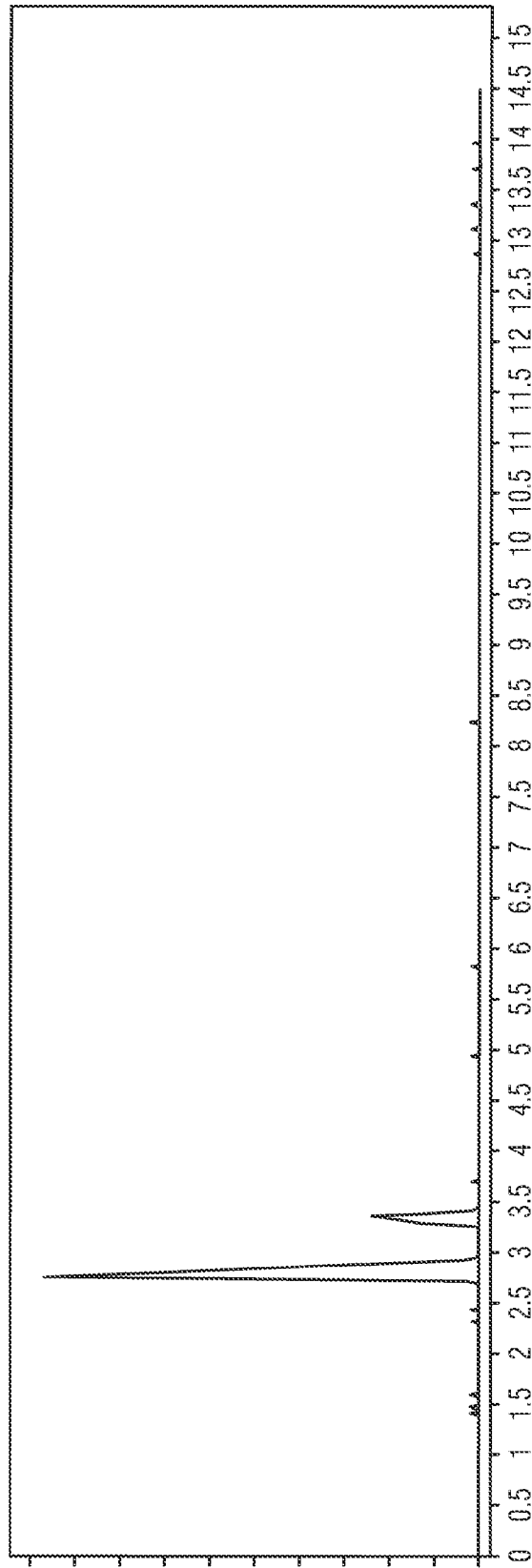
Figure 5D:
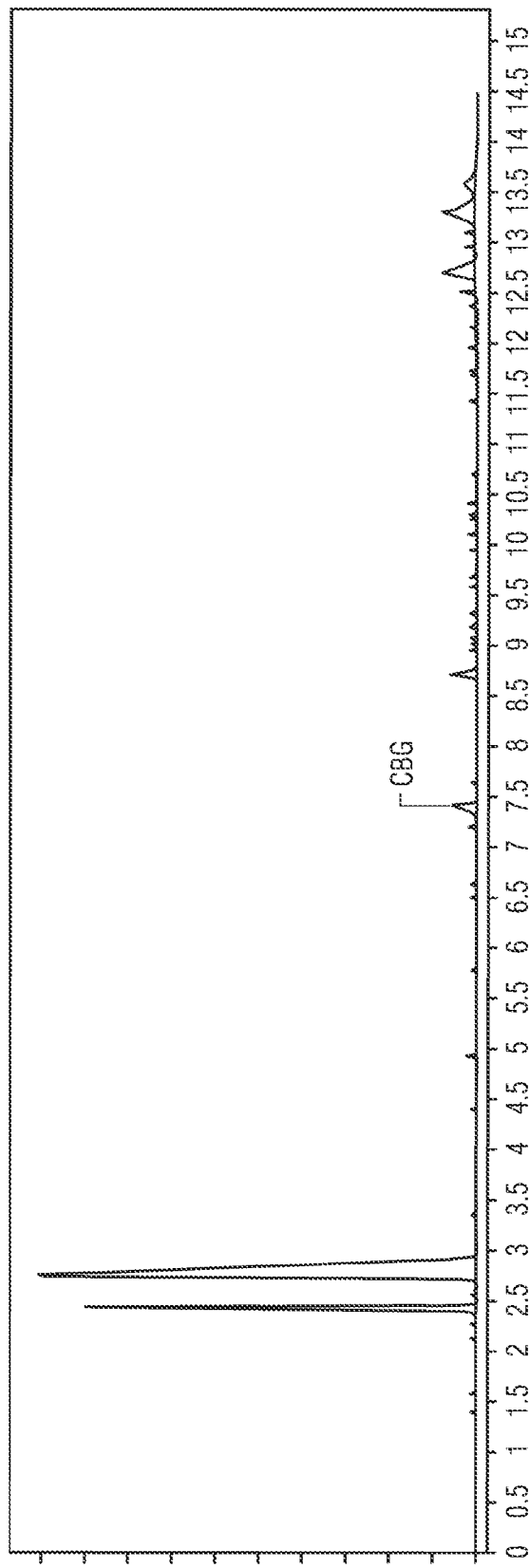
Figure 5E:
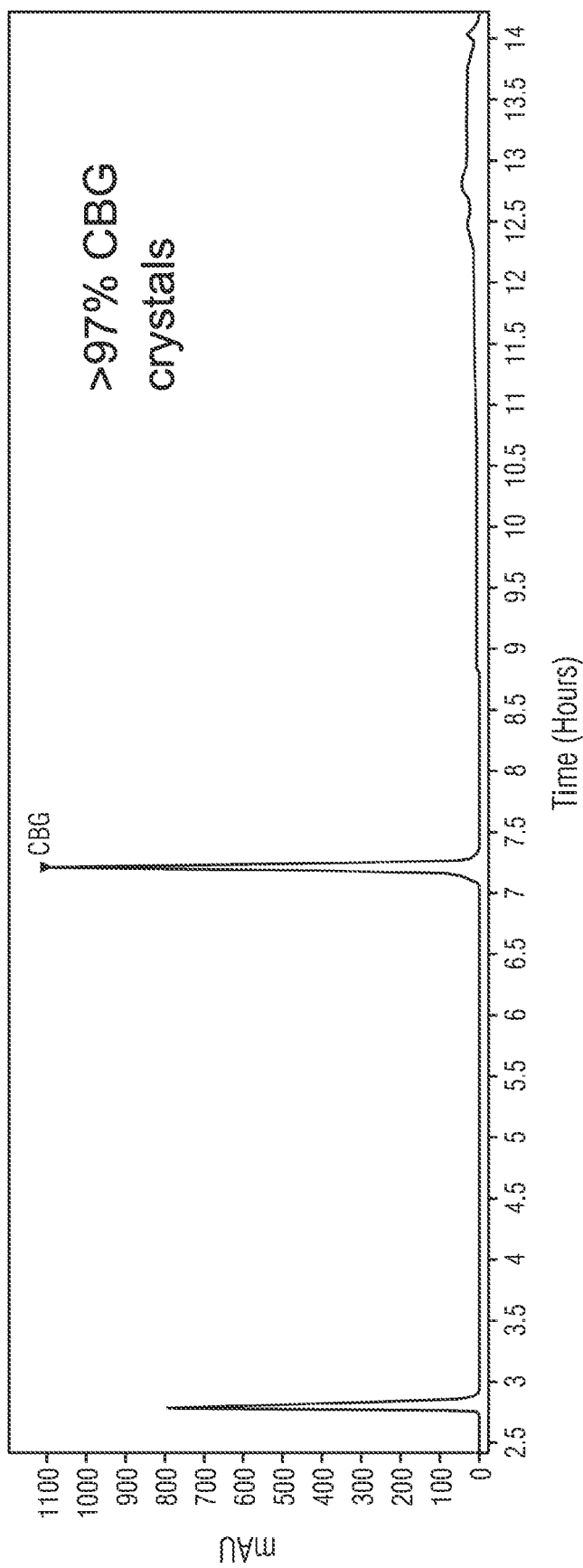

Olivetol (100 g, 555 mmol) was combined with geraniol (145 g, 944 mmol) in 4 L chloroform. To the mixture was added p-toluenesulfonic acid monohydrate (5.5 mmol). The reaction mixture was stirred at room temperature in the dark for 14 hours. The mixture was washed thoroughly with saturated aqueous $NaHCO_3$. The organic layer was washed with water, dried over anhydrous sodium sulfate, and the solvent removed at 40° C. under reduced pressure to give 250 g dark brown oil. A 30.8 g portion of this mixture was purified in the following way: batch fractional distillation under reduced pressure was used, to obtain 8.5 g amber oil containing CBG in approximately 40% wt/wt purity. During the distillation, olivetol and geraniol were recovered in high purity. The distilled CBG was crystallized from heptane solution (1:2 w/w ratio) at −8° C. and the purified CBG was isolated as colourless crystals (1.7 g, ~8% yield based on olivetol). HPLC chromatograms of the fractions from distillation are shown in FIGS. 5A-5E. Specifically, FIG. 5A shows a chromatogram of a product mixture comprising about 20% CBG provided by the methods disclosed herein. FIG. 5B shows a chromatogram of the distillate obtained from the product mixture comprising about 40% CBG. FIGS. 5C and 5D show chromatograms of recovered geraniol and olivetol, respectively. FIG. 5E shows a chromatogram of CBG crystals after separation from the product mixture and crystallization.

Example 5

Figure 6:
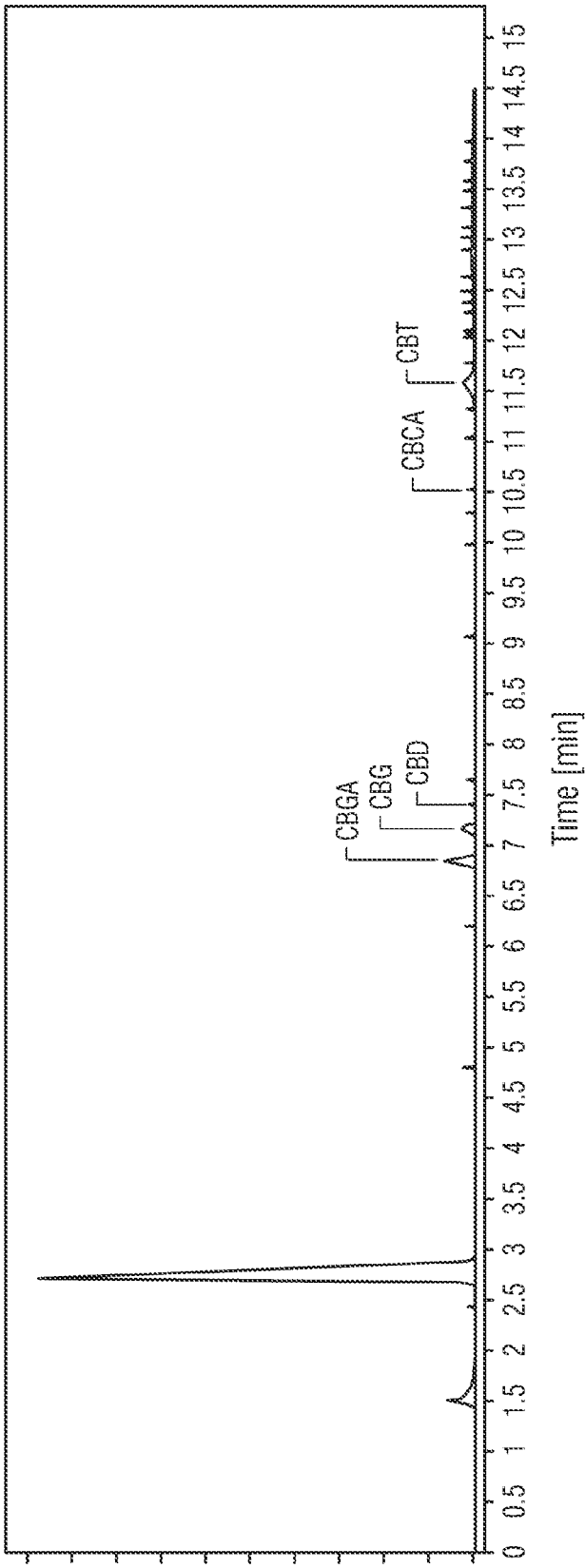
FIG. 6 shows HPLC with diode array detector (HPLC-DAD) of the reaction mixture at the end of the set of reaction conditions provided by a method of the present disclosure. The reaction mixture comprises about 90% CBGA and about 10% CBG.

To a flask equipped with a magnetic stir bar, containing CBG (58 mg, 0.183 mmol, 1.0 equiv.) was added a 2.0 M solution of methyl magnesium carbonate (0.505 ml, 1.01 mmol, 5.5 equiv.) in dimethylformamide (DMF) under $CO_2$ atmosphere. The mixture was heated to 120° C. and stirred for 2.5 h. The mixture was cooled to room temperature, and carefully quenched with an excess of a 10% wt solution of citric acid in water, and diluted with 5 ml methyl tert-butyl ether (MTBE). Once the solids were fully dissolved, the organic layer was washed with 3×5 ml water, and the solvent evaporated under reduced pressure to give 118 mg pink solid. HPLC analysis showed this solid contained 54% wt CBGA (~85% yield), and 9% wt (FIG. 6).

Example 6

To a flask equipped with a magnetic stir bar, containing CBG (1.640 g, 5.182 mmol, 1.0 equiv.) under $CO_2$ atmosphere was added a 2.0 M solution of methyl magnesium carbonate (8.0 ml, 16 mmol, 3.1 equiv.) in dimethylformamide (DMF). The mixture was heated to 120° C. and stirred for 3 h. The mixture was cooled to room temperature, diluted with about 15 ml of 1:1 MeOH:water, and carefully quenched with an excess of a 50% wt solution of citric acid in water. Once the solids were fully dissolved, the mixture was extracted with about 2×10 ml methyl tert-butyl ether (MTBE), and the combined organic layers were washed with 3×10 ml water. The solvent was evaporated under reduced pressure to give 2.046 g red-brown oil. The mixture was dissolved in heptane with a few drops of acetone, concentrated under reduced pressure to about 10 ml volume, and crystallized slowly at 4° C. to yield 222 mg bright orange crystals of CBGA. Concentrating the mother liquor produced a further 261 mg light tan coloured crystals. HPLC analysis showed both crops of crystals to be pure CBGA (483 mg total, 25% isolated yield)

In the present disclosure, all terms referred to in singular form are meant to encompass plural forms of the same. Likewise, all terms referred to in plural form are meant to encompass singular forms of the same. Unless defined otherwise, all technical and scientific terms used herein have the same meaning as commonly understood by one of ordinary skill in the art to which this disclosure pertains.

As used herein, the term "about" refers to an approximately +/−10% variation from a given value. It is to be understood that such a variation is always included in any given value provided herein, whether or not it is specifically referred to.

It should be understood that the compositions and methods are described in terms of "comprising," "containing," or "including" various components or steps, the compositions and methods can also "consist essentially of or "consist of the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Although individual embodiments are discussed, the disclosure covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

Many obvious variations of the embodiments set out herein will suggest themselves to those skilled in the art in light of the present disclosure. Such obvious variations are within the full intended scope of the appended claims.

The invention claimed is:

1. A method for preparing cannabigerolic acid (CBGA) or a CBGA analog, the method comprising:
    reacting geraniol with a compound (I) of the following structure:

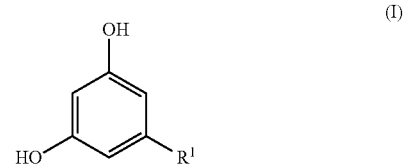

wherein $R^1$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl), $(C_0$-$C_4$ alkyl)-$NR^{2a}R^{2b}$, $(C_0$-$C_4$ alkyl)-aryl, $(C_0$-$C_4$ alkyl)-heteroaryl, $(C_0$-$C_4$ alkyl)-cycloalkyl, or $(C_0$-$C_4$ alkyl)-heterocycloalkyl, wherein $R^{2a}$ and $R^{2b}$ are each independently hydrogen or $C_1$-$C_6$ alkyl;
    in the presence of an acid catalyst and optionally a solvent to form a cannabigerol (CBG) or a CBG analog, wherein the acid catalyst is acidic alumina, iron (III) perchlorate hydrate, or a combination thereof; and
    reacting the CBG or CBG analog with methylmagnesium carbonate to provide the CBGA or CBGA analog.

2. The method of claim 1, wherein the acid catalyst is acidic alumina.

3. The method of claim 1, wherein the acid catalyst iron (III) perchlorate hydrate.

4. The method of claim 1, wherein the compound (I) and geraniol are present in a compound (II):geraniol molar ratio of between 10:1 and 1:10.

5. The method of claim 1, wherein $R^1$ is $C_1$-$C_{12}$ alkyl.

6. The method of claim 1, wherein $R^1$ is $C_3H_7$ or $C_7H_{15}$.

7. The method of claim 1, wherein $R^1$ is $C_5H_{11}$.

8. The method of claim 1, wherein the solvent is present.

9. The method of claim 8, wherein the solvent is chloroform, heptane, tert butylmethyl ether, diethyl ether, dichloromethane, dichloroethane, trifluorotoluene, hexane, cyclohexane, pentane, toluene, or any combination thereof.

10. A method for preparing cannabigerolic acid (CBGA) or a CBGA analog, the method comprising:

reacting geraniol with a compound (II) of the following structure:

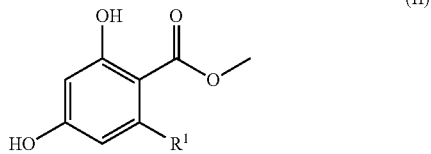

(II)

wherein $R^1$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl$)$, $(C_0$-$C_4$ alkyl$)$-$NR^{2a}R^{2b}$, $(C_0$-$C_4$ alkyl$)$-aryl, $(C_0$-$C_4$ alkyl$)$-heteroaryl, $(C_0$-$C_4$ alkyl$)$-cycloalkyl, or $(C_0$-$C_4$ alkyl$)$-heterocycloalkyl, wherein $R^{2a}$ and $R^{2b}$ are each independently hydrogen or $C_1$-$C_6$ alkyl;

in the presence of an acid catalyst and optionally a solvent, wherein the acid catalyst is camphorsulfonic acid, acidic alumina, montmorillonite K10, iron (III) perchlorate hydrate, or a combination thereof; and hydrolyzing with one or more mild hydrolysis reagents to provide the CBGA or CBGA analog.

11. The method of claim 10, wherein the compound (II) and geraniol are present in a compound (II):geraniol molar ratio of between 10:1 and 1:10.

12. The method of claim 10, wherein $R^1$ is $C_1$-$C_{12}$ alkyl.

13. The method of claim 10, wherein the reacting step is performed with heating.

14. The method of claim 10, wherein the solvent is present.

15. The method of claim 14, wherein the solvent is chloroform, heptane, tert butylmethyl ether, diethyl ether, dichloromethane, dichloroethane, trifluorotoluene, hexane, cyclohexane, pentane, toluene, or any combination thereof.

16. A method for preparing cannabigerolic acid (CBGA) or a CBGA analog, the method comprising:

reacting geraniol with a compound (II) of the following structure:

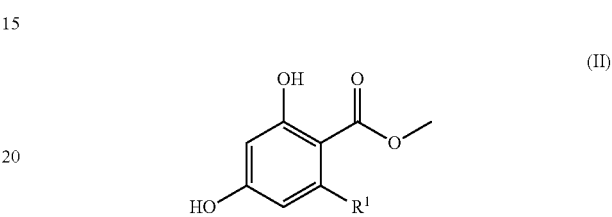

(II)

wherein $R^1$ is hydrogen, $C_1$-$C_{12}$ alkyl, $C_2$-$C_{12}$ alkenyl, $C_2$-$C_{12}$ alkynyl, $(OCH_2CH_2)_{0-6}O(C_1$-$C_8$ alkyl$)$, $(C_0$-$C_4$ alkyl$)$-$NR^{2a}R^{2b}$, $(C_0$-$C_4$ alkyl$)$-aryl, $(C_0$-$C_4$ alkyl$)$-heteroaryl, $(C_0$-$C_4$ alkyl$)$-cycloalkyl, or $(C_0$-$C_4$ alkyl$)$-heterocycloalkyl, wherein $R^{2a}$ and $R^{2b}$ are each independently hydrogen or $C_1$-$C_6$ alkyl;

in the presence of acidic alumina and a solvent, wherein the compound (II) and geraniol are present in a compound (II):geraniol molar ratio of between 10:1 and 1:10; and hydrolyzing with one or more mild hydrolysis reagents to provide the CBGA or CBGA analog.

17. The method of claim 16, wherein the reacting step is performed with heating.

18. The method of claim 16, wherein the solvent is chloroform, heptane, tert butylmethyl ether, diethyl ether, dichloromethane, dichloroethane, trifluorotoluene, hexane, cyclohexane, pentane, toluene, or any combination thereof.

19. The method of claim 16, wherein $R^1$ is $C_1$-$C_{12}$ alkyl.

* * * * *